US012649701B2

(12) United States Patent
Mendenhall et al.

(10) Patent No.: US 12,649,701 B2
(45) Date of Patent: Jun. 9, 2026

(54) GAS GENERANT COMPOSITIONS COMPRISING MELAMINE OXALATE FOR USE IN AUTOMOTIVE RESTRAINT DEVICES

(71) Applicant: AUTOLIV ASP, INC., Ogden, UT (US)

(72) Inventors: Ivan V. Mendenhall, Providence, UT (US); Gary K. Lund, Malad City, ID (US)

(73) Assignee: AUTOLIV ASP, INC., Ogden, UT (US)

( * ) Notice: Subject to any disclaimer, the term of this patent is extended or adjusted under 35 U.S.C. 154(b) by 1471 days.

(21) Appl. No.: 16/369,577

(22) Filed: Mar. 29, 2019

(65) Prior Publication Data

US 2020/0308077 A1 Oct. 1, 2020

(51) Int. Cl.

| | |
|---|---|
| ***C06B 25/34*** | (2006.01) |
| ***C06B 41/00*** | (2006.01) |
| ***C06B 43/00*** | (2006.01) |
| ***C07C 55/07*** | (2006.01) |
| ***C07D 251/54*** | (2006.01) |

(52) U.S. Cl.

CPC .............. *C06B 25/34* (2013.01); *C06B 41/00* (2013.01); *C06B 43/00* (2013.01); *C07C 55/07* (2013.01); *C07D 251/54* (2013.01)

(58) Field of Classification Search

None

See application file for complete search history.

(56) References Cited

U.S. PATENT DOCUMENTS

| | | | | |
|---|---|---|---|---|
| 2,769,731 | A | 11/1956 | Schneid | |
| 3,473,981 | A | 10/1969 | Butts et al. | |
| 3,862,866 | A | 1/1975 | Timmerman et al. | |
| 4,099,376 | A | 7/1978 | Japs | |
| 6,039,820 | A | 3/2000 | Hinshaw et al. | |
| 6,051,158 | A | 4/2000 | Taylor et al. | |
| 6,241,281 | B1 | 6/2001 | Hinshaw et al. | |
| 6,602,365 | B1 | 8/2003 | Mendenhall | |
| 6,958,101 | B2 | 10/2005 | Mendenhall et al. | |
| 8,231,747 | B2 | 7/2012 | Mendenhall et al. | |
| 2003/0089883 | A1 | 5/2003 | Knowlton et al. | |
| 2003/0094225 | A1 | 5/2003 | Knowlton et al. | |
| 2004/0231767 | A1 | 11/2004 | Mendenhall et al. | |
| 2005/0127324 | A1* | 6/2005 | Wu | C06B 23/04 252/181.3 |
| 2007/0131900 | A1 | 6/2007 | Wu | |
| 2011/0025030 | A1* | 2/2011 | Mendenhall | C06B 21/0083 427/372.2 |
| 2013/0139935 | A1 | 6/2013 | Baggett, Jr. et al. | |
| 2014/0261927 | A1 | 9/2014 | Mendenhall et al. | |
| 2015/0183930 | A1* | 7/2015 | Hsueh | C08K 7/14 524/502 |
| 2017/0218178 | A1 | 8/2017 | Akahira et al. | |
| 2020/0308078 | A1 | 10/2020 | Mendenhall et al. | |
| 2020/0308079 | A1 | 10/2020 | Mendenhall et al. | |

FOREIGN PATENT DOCUMENTS

| | | | | |
|---|---|---|---|---|
| EP | 0400402 | * | 5/1990 | E04B 1/94 |
| EP | 3000799 | A1 | 3/2016 | |
| GB | 2200915 | A | 8/1988 | |
| JP | 2006076832 | A | 3/2006 | |
| JP | 2006290699 | A | 10/2006 | |
| JP | 2007-535977 | A | 12/2007 | |
| JP | 2008260658 | A | 10/2008 | |
| RU | 2247700 | C2 | 3/2005 | |

OTHER PUBLICATIONS

Mendenhall, Ivan V. et al., U.S. Appl. No. 16/369,591, filed Mar. 29, 2019 entitled, "Gas Generant Compositions Comprising a Thermally Stable Crystalline Hydrate Compound for Cooling Combustion Flame Temperature and Improving Ballistic Performance," 57 pages.

Mendenhall, Ivan V. et al., U.S. Appl. No. 16/369,609, filed Mar. 29, 2019 entitled, "Cool Burning Hydrate Fuels in Gas Generant Formulations for Automotive Airbag Applications," 43 pages.

International Search Report and Written Opinion for International Application No. PCT/US2020/017591 mailed May 28, 2020, 11 pages (ISA/EP).

International Search Report and Written Opinion for International Application No. PCT/US2020/017584 mailed Jun. 16, 2020, 10 pages (ISA/EP).

International Search Report and Written Opinion for International Patent Application No. PCT/US2020/017595 mailed Jul. 1, 2020, 13 pages (ISA/EP).

Office Action received from the Japanese Patent Office in corresponding application JP2021-555209 dated Oct. 25, 2022, and its English translation.

Structural and comparative electrochemical study of M(II) oxalates, M=Mn, Fe, Co, Ni, Cu, Zn, Maria C. Lopez, J. L. Tirado, C.Perez Vicente, Journal of Power Sources vol. 227, Apr. 1, 2013, pp. 65-71 (Year: 2013).

Crystal structure of the copper complex with cyanuric acid Cu(C3H2N303)2(H20)2 Author Chang-Zhang Chen Chen, Chang-Zhang (Year: 1995).

* cited by examiner

*Primary Examiner* — Aileen B Felton

(74) *Attorney, Agent, or Firm* — Harness, Dickey & Pierce, P.L.C.

(57) ABSTRACT

A gas generant composition for passive inflatable restraint systems (e.g., airbags) for automobiles is provided that comprises a melamine oxalate compound. The gas generant may be a cool burning gas generant composition that comprises a melamine oxalate compound, a co-fuel, such as guanidine nitrate, and an oxidizer, such as basic copper nitrate. The gas generant composition has advantageous combustion properties, including a maximum flame temperature at combustion ($T_c$) of ≤about 1700K (1,427° C.), a linear burn rate of ≥about 18 mm per second at a pressure of about 10 megapascals (MPa), a gas yield of the gas generant composition of ≥about 5.7 moles/100 $cm^3$, and a linear burn rate pressure exponent of ≤about 0.35.

11 Claims, No Drawings

GAS GENERANT COMPOSITIONS COMPRISING MELAMINE OXALATE FOR USE IN AUTOMOTIVE RESTRAINT DEVICES

FIELD

The present disclosure relates to cool burning gas generant compositions for inflatable restraint systems in automobiles.

BACKGROUND

This section provides background information related to the present disclosure which is not necessarily prior art.

Passive inflatable restraint systems have been used for over twenty-five years in various applications, such as automobiles. Certain types of passive inflatable restraint systems minimize occupant injuries by using a pyrotechnic gas generant to inflate an airbag cushion (e.g., gas initiators and/or inflators) or to actuate a seatbelt tensioner (e.g., micro gas generators), for example. Automotive airbag inflator performance and safety requirements are continually increasing to enhance passenger safety, while concurrently striving to increase functionality and reduce manufacturing costs.

Suitable gas generants provide sufficient gas mass flow in a desired time interval to achieve a required work impulse for the inflating device. One way of optimizing gas generant performance and reducing system cost is to reduce the combustion flame temperature of the gas generant formulation. This may seem counterintuitive because gas temperature influences the amount of work the generant gases can do. However, high gas temperatures can be undesirable because burns and related thermal damage can result. In addition, high gas temperatures can also lead to an excessive reliance or sensitivity of the gas to heat transfer and excessively rapid deflation profiles, which can be undesirable. In order to mitigate the effects of high combustion flame temperatures (for example, a high flame temperature may be considered anything in excess of 1700K at combustion), a significant portion of the mass of an inflator is often relegated to heat sink in combination with filtration systems. This detrimentally impacts the weight of the inflator and thus the efficiency of the system.

In addition to combustion flame temperature, two other important gas generant characteristics that help to improve the efficiency of the inflator (and thus its size and weight) are the gas yield of the gas generant (for example, measured in moles/100 grams of formulation) and the ability of the solid combustion products to stay in a large consolidated mass that is easily filtered from the gas stream (slaggability). Hence, for new advanced inflator designs, it is desirable to reduce or minimize filter components and heat sink requirements as much as possible. As part of these new designs, new cool burning gas generant formulations are advantageous because they reduce heat sink requirements and improve performance.

SUMMARY

This section provides a general summary of the disclosure, and is not a comprehensive disclosure of its full scope or all of its features.

Advantageously, the present disclosure in certain variations provides a gas generant composition for an automotive inflatable restraint system comprising a melamine oxalate compound.

In one aspect, the melamine oxalate compound comprises a molar ratio of melamine to oxalic acid ranging from about 1:1 to about 2:3.

In one aspect, the melamine oxalate compound is selected from the group consisting of: melamine monoxalate, dimelamine trioxalate, and combinations thereof.

In one aspect, the gas generant composition has a linear burn rate of greater than or equal to about 18 mm per second at a pressure of about 10 megapascals (MPa).

In one aspect, the gas generant composition has a linear burn rate pressure exponent of less than or equal to about 0.35.

In one aspect, the gas generant composition has a maximum flame temperature at combustion ($T_c$) of less than or equal to about 1700K (1,427° C.).

In one aspect, the gas generant composition has a maximum flame temperature at combustion ($T_c$) of greater than or equal to about 1400K (1,127° C.) to less than or equal to about 1600K (1,327° C.).

In one aspect, the gas generant composition has a gas yield of the gas generant of greater than or equal to about 5.7 moles/100 $cm^3$.

Advantageously, the present disclosure in certain other variations provides a cool burning gas generant composition for an automotive inflatable restraint system that comprises a melamine oxalate compound, a co-fuel, and an oxidizer. The gas generant composition has a maximum flame temperature at combustion ($T_c$) of less than or equal to about 1700K (1,427° C.), a linear burn rate of greater than or equal to about 18 mm per second at a pressure of about 10 megapascals (MPa), a gas yield of the gas generant composition of greater than or equal to about 5.7 moles/100 $cm^3$, and a linear burn rate pressure exponent of less than or equal to about 0.35.

In one aspect, the melamine oxalate compound comprises a molar ratio of melamine to oxalic acid ranging from about 1:1 to about 2:3.

In one aspect, the melamine oxalate compound is selected from the group consisting of: melamine monoxalate, dimelamine trioxalate, and combinations thereof.

In one aspect, the gas generant composition has a maximum flame temperature at combustion ($T_c$) of greater than or equal to about 1400K (1,127° C.) to less than or equal to about 1600K (1,327° C.).

In one aspect, the melamine oxalate compound is present at greater than or equal to about 5% by weight to less than or equal to about 30% by weight of the total gas generant composition.

In one aspect, the co-fuel is selected from the group consisting of: guanidine nitrate, diammonium 5,5'-bitetrazole (DABT), copper bis guanylurea dinitrate, hexamine cobalt (III) nitrate, copper diammine bitetrazole, and combinations thereof.

In one aspect, the oxidizer is selected from the group consisting of: basic copper nitrate, alkali metal or alkaline earth metal nitrates, alkali metal, alkaline earth metal, or ammonium perchlorates, metal oxides, and combinations thereof.

In one aspect, the co-fuel comprises guanidine nitrate present at greater than or equal to about 10% to less than or equal to about 50% by weight of the gas generant composition.

In one further aspect, the oxidizer comprising basic copper nitrate is present at greater than or equal to about 30% to less than or equal to about 70% by weight of the gas generant composition.

In one aspect, the melamine oxalate compound is present at greater than or equal to about 5% by weight to less than or equal to about 30% by weight of the total gas generant composition, the co-fuel is present at greater than or equal to about 10% to less than or equal to about 50% by weight of the total gas generant composition; the oxidizer is present at greater than or equal to about 30% to less than or equal to about 70% by weight of the total gas generant composition; and greater than or equal to 0% to less than or equal to about 10% by weight of the total gas generant composition of one or more gas generant additives.

Advantageously, the present disclosure in certain further variations provides a cool burning gas generant composition for an automotive inflatable restraint system comprising a melamine oxalate compound, guanidine nitrate, and basic copper nitrate. The gas generant composition has a maximum flame temperature at combustion ($T_c$) of less than or equal to about 1700K (1,427° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

Further areas of applicability will become apparent from the description provided herein. The description and specific examples in this summary are intended for purposes of illustration only and are not intended to limit the scope of the present disclosure.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of" Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

As used herein, the terms "composition" and "material" are used interchangeably to refer broadly to a substance containing at least the preferred chemical constituents, elements, or compounds, but which may also comprise additional elements, compounds, or substances, including trace amounts of impurities, unless otherwise indicated.

Example embodiments will now be described more fully with reference to the accompanying drawings.

The present disclosure contemplates a composition for gas generant that can be in the form of a solid grain, a pellet, a tablet, or the like. As the gas generant burns it creates a gas or effluent for inflation that is directed to an inflating device (e.g., airbag) within the inflatable restraint system. Various different gas generant compositions are used in vehicular occupant inflatable restraint systems. Gas generant material selection involves various factors, including meeting current industry performance specifications, guidelines and standards, generating safe gases or effluents, handling safety of the gas generant materials, durational stability of the materials, and cost-effectiveness in manufacture, among other considerations. It is preferred that the gas generant compositions are safe during handling, storage, and disposal, and preferably are azide-free.

In various aspects, the gas generant typically includes at least one fuel component and at least one oxidizer component, and may include other minor ingredients, that once ignited combust rapidly to form gaseous reaction products (e.g., $CO_2$, $H_2O$, and $N_2$). One or more fuel compounds undergo rapid combustion to form heat and gaseous products; e.g., the gas generant burns to create heated inflation gas for an inflatable restraint device or to actuate a piston. The gas-generating composition also includes one or more oxidizing components, where the oxidizing component reacts with the fuel component in order to generate the gas product. "Slag" or "clinker" is another name for solid combustion products formed during combustion of the gas generant material. Ideally, the slag will maintain the original shape of the gas generant (e.g., grain, pellet, or tablet) and be large and easily filtered. This is particularly important when the inflator design includes a reduced mass filtration system for the purpose of reducing the inflator size and weight such as can be used with cool burning gas generant formulations.

Advanced inflator design concepts incorporate reduced filter and heat sink mass. Use of cool burning gas generant formulations reduces heat sink requirements. Additionally, because filter mass is reduced, it is desirable to have a cool burning gas generant that slags very well. By "slagging," it is meant that certain solid combustion products generated during burning of the gas generant form a large integral solid mass that is retained inside the combustion chamber during combustion, rather than passing through the filter into the airbag. Slagging agents can be used to achieve this effect. A slagging agent is a compound or material, usually inert to combustion, that melts at combustion temperatures and agglomerates or collects all of the solid combustion products together. Examples of conventional slagging agents are silicon dioxide, aluminum oxide, glass and other metal oxides that melt at or near the combustion flame temperature.

As noted above, one way of optimizing gas generant performance and reducing system cost of gas generants for passive restraint systems is to reduce the combustion flame temperature of the gas generant formulation. In an efficient inflator design, the amount of screen pack used would be sufficient to filter the gas stream and to cool the gas stream from combustion for a desired quantity of gas generant to a desired temperature before entering an airbag. The desired combustion flame temperature for a gas generant formulation used in a frontal automotive inflator application is in a range of greater than or equal to about 1400K (1,127° C.) to less than or equal to 1900K (1,627° C.). In addition to combustion flame temperature, as noted above, two other important gas generant characteristics that help to improve the efficiency of the inflator and thus its size and weight are the gas yield of the gas generant and the ability of the solid combustion products to form a slag and thus stay in a large consolidated mass that is easily filtered from the gas stream.

One current way to obtain cool burning gas generant formulations is to use large particle endothermic coolants, such as aluminum hydroxide, which is described in co-owned U.S. Patent Publication No. 2014/0261927 entitled "Enhanced Slag Formation For Copper-Containing Gas Generants," the relevant portions of which are incorporated herein. The large particle size of the aluminum hydroxide allows it to be used at high levels (e.g., about 10-20%) without adversely affecting the burning rate of the overall gas generant formulation. In addition, decomposition of aluminum hydroxide releases water vapor, which participates in inflation of the airbag and helps to maintain a high gas yield from the gas generant formulation. These formulations slag very well. Although use of aluminum hydroxide is an effective technique for cooling a gas generant, the ballistic performance of the formulation is quite sensitive to the particle size distribution of the aluminum hydroxide coolant, thus requiring strict control of the particle size distribution to minimize variation from batch to batch.

The present disclosure provides alternative cool burning gas generant compositions that allow low flame temperatures at combustion (e.g., ≥about 1400K (1,127° C.) to ≤about 1600K (1,327° C.)) to be obtained while maintaining good performance, especially those that can employ certain fuel and oxidizer combinations, like basic copper nitrate and guanidine nitrate. In various aspects, the present disclosure contemplates a gas generant composition comprising a melamine oxalate compound. As discussed further below, the melamine oxalate compound participates in combustion (e.g., as a fuel) and can eliminate the need to use a large particle size endothermic coolant. Further, the melamine oxalate compound has a high cooling capacity, which allows relatively small amounts of the compound to cool the formulation to desired temperatures, thereby maintaining a high gas yield. While other cool burning co-fuels would appear to potentially meet these requirements for a cool burning gas generant, many of these alternative options do not provide a formulation that has desirable ballistic characteristics, including exhibiting insufficient linear burn rate, excessive pressure sensitivity of burn rate, low burn rates, and/or insufficient gas yields. However, in accordance with the present disclosure, melamine oxalate serves as a co-fuel that can fulfill all of these performance criteria to provide cool burning gas generant compositions.

Melamine, which is slightly basic, and oxalic acid react to form a salt compound. The compound formed depends on the ratio of melamine to oxalic acid present. A 1:1 molar ratio of melamine to oxalic acid forms melamine monoxalate, represented by the structure:

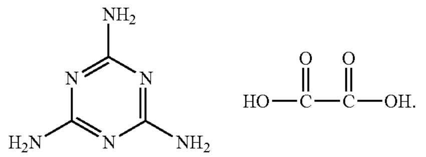 [SMILES: Nc1nc(N)nc(N)n1 ; O=C(O)C(=O)O]

The CAS number for melamine monoxalate is 67797-68-6.

A 2:3 (alternatively 1:1.5) molar ratio of melamine to oxalic acid forms dimelamine trioxalate represented by the structure:

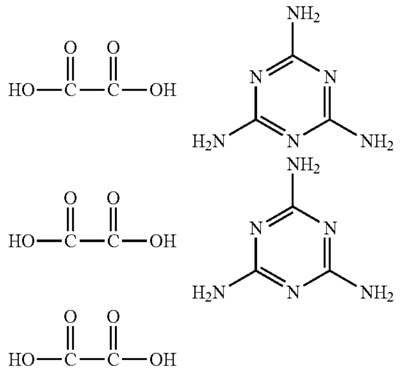

The CAS number for trimelamine trioxalate is 8214-01-4. In certain aspects, the melamine oxalate compound may have combinations of these respective salts so that the ratio of melamine to oxalic acid may range from about 1:1 to about 2:3.

Thus, in various aspects, the present disclosure contemplates a gas generant composition including a melamine oxalate compound selected from the group consisting of: melamine monoxalate, dimelamine trioxalate, and combinations thereof. As discussed further herein, inclusion of the melamine oxalate compound in a gas generant composition provides not only a cool burning formulation, but also one that meets certain desirable ballistic properties, including by way of non-limiting example, high gas yield, suitable linear burn rates, and minimal burn rate sensitivity to pressure.

In various aspects, the present disclosure provides a relatively cool burning gas generant composition that comprises a melamine oxalate compound as a co-fuel. The gas generant composition may also comprise a primary fuel, along with at least one oxidizer. A cool burning gas generant having combustion flame temperatures of less than approximately 1700K (1,427° C.) has been shown to enable inflator devices with reduced filtration, which operate in a manner that provides adequate restraint and protection, without the risk of burns or injury to an automobile occupant in the event of a crash. Thus, minimizing flame temperature is advantageous. In certain aspects of the present technology, a high flame temperature may be considered anything in excess of about 1700K (1,427° C.) at combustion and in certain variations, anything in excess of about 1600K (1,327° C.).

In certain aspects, the gas generant composition is a cool burning formulation having a maximum flame temperature at combustion ($T_c$) of less than or equal to about 1700K (1,427° C.), optionally less than or equal to about 1600K (1,327° C.), and in certain other aspects, optionally within a range of greater than or equal to about 1400K (1,127° C.) to less than or equal to 1600K (1,327° C.). A melamine oxalate compound is combusted during the decomposition reaction of the gas generant and thus, the melamine oxalate compound decomposes within this temperature range.

Thus, in accordance with various aspects of the present teachings, an improved cool burning gas generant composition is provided that includes a melamine oxalate compound and has a volumetric gas yield of optionally greater than or equal to about 5.7 moles/100 $cm^3$ of gas generant. The product of gravimetric gas yield and density is a volumetric gas yield. In other embodiments, the volumetric gas yield is greater than or equal to about 5.9 moles/100 $cm^3$ of gas generant, optionally greater than or equal to about 6.0 moles/100 $cm^3$ of gas generant, optionally greater than or equal to about 6.1 moles/100 $cm^3$ of gas generant, and in certain variations, optionally greater than or equal to about 6.2 moles/100 $cm^3$ of gas generant.

In addition to improved gas generant performance with respect to volumetric gas yield, relative quickness as determined by observed burning rate is also important in inflator gas generant design. In general, a burn rate for a gas generant composition can be represented by a simplified equation:

$$r_b=k(P)^n \qquad (1)$$

where $r_b$ is burn rate (linear); k is a constant; P is pressure, and n is a pressure exponent, where the pressure exponent is the slope of a linear regression line drawn through the log-log plot of linear burn rate ($r_b$) versus pressure (P).

In various embodiments, the gas generant has a desirably high burning rate which enables desirable pressure curves for inflation of an airbag. A linear burn rate "$r_b$" for a gas generant material may be expressed in length per time at a given pressure. In accordance with various aspects of the present disclosure, the gas generant has a linear burn rate of greater than or equal to about 18 mm per second at a pressure of about 10 megapascals (MPa). In certain embodiments, the burn rate for the gas generant is greater than or equal to about 19 mm per second at a pressure of about 10 MPa, optionally greater than or equal to about 20 mm per second at a pressure of about 10 MPa, optionally greater than or equal to about 21 mm per second at a pressure of about 10 MPa, optionally greater than or equal to about 22 mm per second at a pressure of about 10 MPa, and in certain variations, optionally greater than or equal to about 23 mm per second at a pressure of about 10 MPa.

Another important aspect of a gas generant material's performance is combustion stability, as reflected by its burn rate pressure sensitivity, which is related to the pressure exponent or the slope of the linear regression line of the logarithmic-logarithmic plot of burn rate ($r_b$) versus pressure (P). It is generally desirable to develop gas generant materials that exhibit reduced or lessened burn rate pressure sensitivity, as gas generant materials exhibiting higher burn rate pressure sensitivity can potentially lead to undesirable performance variability, such as when the corresponding material or formulation is reacted under different pressure conditions. As referred to herein, "pressure sensitivity" is meant to refer to undesirable pressure sensitivity of a gas generant over the range of typical operating pressure for a gas inflator, for example, about 1,000 psi (about 6.9 MPa) to about 5,000 psi (about 34.5 MPa) resulting in inflator performance variability. It is desirable to employ gas generant compositions that have relatively consistent performance during combustion, including burn rates that are relatively independent of pressure (e.g., pressure insensitive).

In various aspects, a gas generant composition is provided that has enhanced burning rate performance, and a reduced burn rate pressure sensitivity as it is used in an inflator device. In various aspects, the gas generants of the present disclosure have improved pressure sensitivity (i.e., reduced pressure sensitivity) and enhanced combustion performance, for example, by having reduced linear burn rate pressure sensitivity (i.e., a relatively low pressure exponent (n) or slope of a linear regression line drawn through a log-log plot of burn rate ($r_b$) versus pressure (P)), and higher linear burn rate (i.e., rate of combustion reaction).

In certain aspects, a gas generant material having an acceptable pressure sensitivity has a linear burning rate slope of less than or equal to about 0.35, optionally less than or equal to about 0.3. A material having a burn rate slope of less than or equal to about 0.35 fulfills hot to cold performance variation requirements, and can reduce performance variability and pressure requirements of the inflator as well. Thus, in various aspects, it is desirable that the gas generant materials have a constant slope over the pressure range of inflator operation, which is typically about 1,000 psi (about 6.9 MPa) to about 5,000 psi (about 34.5 MPa) and desirably has a constant slope that is less than or equal to about 0.35.

The cool burning gas generant composition according to various aspects of the present teachings comprise a melamine oxalate compound as a fuel. In certain variations, the melamine oxalate compound is present at greater than or equal to about 5% by weight to less than or equal to about 30% by weight of the total gas generant composition. In other aspects, the melamine oxalate compound is present at greater than or equal to about 10% by weight to less than or equal to about 25% by weight of the total gas generant composition or optionally greater than or equal to about 15% by weight to less than or equal to about 22% by weight of the total gas generant composition.

The cool burning gas generants may also comprise one or more other fuels in addition to the melamine oxalate compound. As appreciated by those of skill in the art, such a fuel component may be combined with additional components in the gas generant, such as co-fuels when multiple fuels are employed or oxidizers. Most fuels known in the art can be used with the present technology and are generally selected to impart certain desirable characteristics to the gas generant formulation, such as gas yield, burning rate, thermal stability, and low cost. These fuels can be organic compounds containing two or more of the elements: carbon (C), hydrogen (H), nitrogen (N), and oxygen (O). The fuels can also include transition metal salts and transition metal nitrate complexes. In certain variations, preferred transition metals are copper and/or cobalt. In accordance with certain aspects of the present teachings, a fuel is selected for the inventive gas generant compositions so that when combusted with certain oxidizers comprising copper, such as basic copper nitrate, a resulting maximum combustion flame temperature ($T_c$) falls within a range of greater than or equal to about 1400K (1,127° C.) to less than or equal to 1600K (1,327° C.).

Examples of fuels useful for gas generants according to the present teachings are selected from the group consisting of guanidine nitrate, diammonium 5,5'-bitetrazole (DABT), copper bis guanylurea dinitrate, hexamine cobalt (III) nitrate, copper diammine bitetrazole, and combinations thereof. Fuels may be used singly or in combination with other co-fuels in addition to the melamine oxalate to impart the desired combustion characteristics. In addition to the melamine oxalate compound, the cool burning gas generant may comprise such additional fuel(s) at greater than or equal to about 10% by weight to less than or equal to about 50% by weight of the total gas generant composition. A suitable cool burning gas generant composition optionally includes a total amount of fuels, including the melamine oxalate compound, of greater than or equal to about 15% to less than or equal to about 80% by weight, optionally greater than or equal to about 25% to less than or equal to about 70%, optionally greater than or equal to about 30% to less than or equal to about 55% of all fuel components in the total gas generant composition.

As appreciated by those of skill in the art, such fuel components may be combined with additional components in the gas generant, such as co-fuels or oxidizers. For example, in certain embodiments, a gas generant composition comprises a substituted basic metal nitrateoxidizer, as described above, and a nitrogen-containing co-fuel like guanidine nitrate. Examples of gas generant compositions having suitable burn rates, density, and gas yield for inclusion in the gas generants of the present disclosure include those described in U.S. Pat. No. 6,958,101 to Mendenhall et al., the relevant portion of which is herein incorporated by reference. The desirability of use of various co-fuels, such as guanidine nitrate or diammonium 5,5'-bitetrazole (DABT), in the gas generant compositions of the present disclosure is generally based on a combination of factors, such as burn rate, cost, stability (e.g., thermal stability), availability and compatibility (e.g., compatibility with other standard or useful pyrotechnic composition components).

Thus, certain suitable oxidizers for the gas generant compositions of the present disclosure include, by way of non-limiting example, alkali metal (e.g., elements of Group 1 of IUPAC Periodic Table, including Li, Na, K, Rb, and/or Cs), alkaline earth metal (e.g., elements of Group 2 of IUPAC Periodic Table, including Be, Ng, Ca, Sr, and/or Ba), and ammonium nitrates, nitrites, and perchlorates; metal oxides (including Cu, Mo, Fe, Bi, La, and the like); basic metal nitrates (e.g., elements of transition metals of Row 4 of IUPAC Periodic Table, including Mn, Fe, Co, Cu, and/or Zn); transition metal complexes of ammonium nitrate (e.g., elements selected from Groups 3-12 of the IUPAC Periodic Table); metal ammine nitrates, metal hydroxides, and combinations thereof. One or more co-fuel/oxidizers are selected along with the fuel component to form a gas generant that upon combustion achieves an effectively high burn rate and gas yield from the fuel. One non-limiting, specific example of a suitable oxidizer includes basic copper nitrate. The gas generant may include combinations of oxidizers, such that the oxidizers may be nominally considered a primary oxidizer, a second oxidizer, and the like.

Oxidizing agents may be respectively present in a gas generant composition in an amount of less than or equal to about 60% by weight of the gas generating composition; optionally less than or equal to about 50% by weight; optionally less than or equal to about 40% by weight; optionally less than or equal to about 30% by weight; optionally less than or equal to about 25% by weight; optionally less than or equal to about 20% by weight; and in certain aspects, less than or equal to about 15% by weight of the gas generant composition.

In certain variations of the present disclosure, the gas generant composition comprises a total amount of oxidizers of greater than or equal to about 30% to less than or equal to about 70% by weight and in certain variations, optionally greater than or equal to about 35% to less than or equal to about 60% by weight of the total gas generant composition. Where a secondary oxidizer, such as a perchlorate, is included in combination with a primary oxidizer, such as basic copper nitrate, it may be limited to an amount of greater than or equal to about 1% by weight to less than or equal to about 10% by weight of the total gas generant composition to retain the cool burning properties of the gas generant.

In certain embodiments, a cool burning gas generant comprises a melamine oxalate compound, a co-fuel, and an oxidizer. The gas generant composition has a maximum flame temperature at combustion ($T_c$) of less than or equal to about 1700K (1,327° C.). The gas generant has a linear burn rate of greater than or equal to about 18 mm per second at a pressure of about 10 megapascals (MPa). Further, the gas generant has a gas yield of the gas generant composition of greater than or equal to about 5.7 moles/100 $cm^3$. The gas generant also has a linear burn rate pressure exponent of less than or equal to about 0.35.

In certain aspects, a cool burning gas generant composition comprises a melamine oxalate compound, guanidine nitrate; and basic copper nitrate. The gas generant composition has a maximum flame temperature at combustion ($T_c$) of less than or equal to about 1700K (1,427° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

In yet other aspects, a cool burning gas generant composition comprises a melamine oxalate compound, at least one co-fuel component mixed with one or more oxidizers, such as a primary oxidizer and a secondary oxidizer comprising a perchlorate-containing oxidizer. By way of example, a co-fuel may include guanidine nitrate, and an oxidizer selected from the group consisting of: basic copper nitrate, alkali metal or alkaline earth metal nitrates, alkali metal, alkaline earth metal, or ammonium perchlorates, metal oxides, and combinations thereof. A particularly suitable oxidizer for the gas generant compositions of the present disclosure is basic copper nitrate. In one variation, an oxidizer may comprise basic copper nitrate as a primary oxidizer and an alkali metal or alkaline earth metal nitrate, or alkali metal, alkaline earth metal, and ammonium perchlorate as a secondary oxidizer.

A gas generant composition may optionally include additional components known to those of skill in the art. Such additives typically function to improve the handling or other material characteristics of the slag which remains after combustion of the gas generant material; and improve ability to handle or process pyrotechnic raw materials. By way of non-limiting example, additional ingredients for the gas generant composition may be selected from the group consisting of: flow aids, pressing aids, metal oxides, and combinations thereof. If minor ingredients or additives are included in the gas generant, they may be cumulatively present at less than or equal to about 10% by weight of the total gas generant composition, optionally less than or equal to about 5% by weight of the total gas generant composition. By way of example, such an additive may be selected from the group consisting of: flow aids, press aids, slagging agents, coolants, metal oxides, and any combinations thereof. Where present in a gas generant composition, in certain variations each respective additive may be present at greater than or equal to 0% to less than or equal to about 4% by weight; optionally greater than or equal to about 0.1% to less than or equal to about 3% by weight, and in certain variations, optionally greater than or equal to about 0.5% to less than or equal to about 1% by weight of the gas generant, so that the total amount of additives is less than or equal to about 4%.

Press aids used during compression processing, include lubricants and/or release agents, such as graphite, calcium stearate, magnesium stearate, molybdenum disulfide, tungsten disulfide, graphitic boron nitride, may be optionally included in the gas generant compositions, by way of non-limiting example. Conventional flow aids may also be employed, such as high surface area fumed silica.

Slag forming agents may be a refractory compound, e.g., aluminum oxide and/or silicon dioxide. Examples of conventional slagging agents are aluminum, silicon, and titanium dioxides, refractory materials or other metal oxides that melt at or near the combustion flame temperature. Coolants for lowering gas temperature include basic copper carbonate or other suitable carbonates.

The gas generant compositions may optionally include a metal oxide that serves as a viscosity-modifying compound or an additional slag-forming agent (in addition to the endothermic slag-forming component described above). Suitable metal oxides may include silicon dioxide, cerium oxide, ferric oxide, titanium oxide, zirconium oxide, bismuth oxide, molybdenum oxide, lanthanum oxide and the like.

In certain aspects, components of the gas generant compositions provided in accordance with the present disclosure may be water soluble or capable of being processed by a slurry that can be spray dried to form granules.

In certain variations, the melamine oxalate compound is present at greater than or equal to about 5% by weight to less than or equal to about 30% by weight of the total gas generant composition, a co-fuel, such as guanidine nitrate, is present at greater than or equal to about 10% to less than or equal to about 50% by weight of the total gas generant composition; an oxidizer, such as basic copper nitrate, is present at greater than or equal to about 30% to less than or equal to about 70% by weight of the total gas generant composition; and greater than or equal to 0% to less than or equal to about 10% by weight of the total gas generant composition of one or more gas generant additives.

In certain variations, the present disclosure contemplates a cool burning gas generant composition for an automotive inflatable restraint system that comprises a melamine oxalate compound, guanidine nitrate, and basic copper nitrate. The gas generant composition has a maximum flame temperature at combustion ($T_c$) of less than or equal to about 1700K (1,427° C.) and in certain aspects, less than or equal to about 1600K (1,327° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

In certain variations, the melamine oxalate compound is present at greater than or equal to about 5% by weight to less than or equal to about 30% by weight of the total gas generant composition, the guanidine nitrate is present at greater than or equal to about 10% to less than or equal to about 50% by weight of the total gas generant composition; the basic copper nitrate is present at greater than or equal to about 30% to less than or equal to about 70% by weight of the total gas generant composition; and one or more gas generant additives are present at greater than or equal to 0% to less than or equal to about 10% by weight of the total gas generant composition.

In yet other variations, the present disclosure contemplates a cool burning gas generant composition for an automotive inflatable restraint system that consists essentially of a melamine oxalate compound, guanidine nitrate, a basic copper nitrate, and optionally one or more gas generant additives from the group consisting of: flow aids, press aids, slagging agents, coolants, metal oxides, and any combinations thereof. The gas generant composition has a maximum flame temperature at combustion ($T_c$) of less than or equal to about 1700K (1,427° C.), optionally less than or equal to about 1600K (1,327° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

In certain other variations, the present disclosure contemplates a cool burning gas generant composition for an automotive inflatable restraint system that consists of a melamine oxalate compound, guanidine nitrate, a basic copper nitrate, and optionally one or more gas generant additives selected from the group consisting of: flow aids, press aids, slagging agents, coolants, metal oxides, and any combinations thereof. The gas generant composition has a maximum flame temperature at combustion ($T_c$) of less than or equal to about 1700K (1,427° C.), optionally less than or equal to about 1600K (1,327° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

Various embodiments of the inventive technology can be further understood by the specific examples contained herein. Specific non-limiting Examples are provided for illustrative purposes of how to make and use the compositions, devices, and methods according to the present teachings.

EXAMPLE 1

A comparison of the properties of the formulations containing a melamine oxalate compound and other cool burning co-fuels similar to melamine oxalate are shown in Table 1 below. Six gas generant mixes are prepared with the formulations specified and tested for purposes of comparison. Mixes 1 and 2 contain melamine oxalate at different concentrations. Mixes 3-6 contain alternative co-fuels that appear to provide cool burning gas generants. The slagging agent is glass fibers and the co-oxidizer is ammonium perchlorate. Flame combustion temperature ($T_c$) K, gas yield ($G_n$) in moles/100 g, volumetric gas yield ($G_v$) in moles 100 $cm^3$, mass density, linear burn rate ($R_b$) at 21 MPa, and slope of pressure sensitivity (n) are measured.

The burning rates in Table 1 are lower than the desired burn rate of at least about 18 mm/second; however, the measured burning rates are from hand mixes, which are typically lower than burning rates obtained in the spray dry production process. Thus, the burn rates in Table 1 do not necessarily represent enhanced burn rates that will be achieved from production processes, but are provided for comparison purposes.

TABLE 1

| Property | Mix 1 | Mix 2 | Mix 3 | Mix 4 | Mix 5 | Mix 6 |
|---|---|---|---|---|---|---|
| % bCN | 59.65 | 58.62 | 48.94 | 52.01 | 30.82 | 58.90 |
| % $GuNO_3$ | 20.15 | 18.18 | 39.56 | 30.49 | 37.18 | 24.85 |
| % Co-fuel | 17.70<br>1:1 melamine oxalate (melamine monoxalate) | 20.70<br>2:3 melamine oxalate (dimelamine trioxylate) | 9<br>urea oxalate | 15<br>biuret oxalate | 29.50<br>cupric oxalate | 13.75<br>melamine cyanurate |
| % Slagging Agent | 1 | 1 | 1 | 1 | 1 | 1 |
| % Co-oxidizer | 1.5 | 1.5 | 1.5 | 1.5 | 1.5 | 1.5 |
| $T_c$ K | 1600 | 1600 | 1600 | 1600 | 1600 | 1600 |
| $G_n$ moles/ 100 $cm^3$ | 2.51 | 2.49 | 2.86 | 2.73 | 2.51 | 2.56 |
| Density g/$cm^3$ | 2.33 | 2.32 | 2.13 | 2.16 | 2.23 | 2.27 |
| $G_v$ moles/100 $cm^3$ | 5.85 | 5.78 | 6.09 | 5.90 | 5.60 | 5.81 |
| $R_b$ at 10 MPa mm/sec | 13.82 | 9.69 | 8.72 | 9.15 | 10.71 | 9.77 |
| Slope | 0.350 | 0.314 | 0.469 | 0.386 | 0.331 | 0.352 |

As shown in Table 1, melamine oxalate in Mixes 1 and 2 (having melamine monooxalate and dimelamine trioxylate co-fuels) meets various goals of high gas yield and good ballistic properties at cool combustion flame temperatures. Mix 1 (1:1 melamine: oxalate) has high burn rates and low burn rate slope. While the burning rate of Mix 2 is lower, the burn rate slope is desirably the lowest value of all those tested. For Mixes 3 and 4 having urea oxalate and biuret oxalate as the co-fuel, the pressure sensitivity/slopes are too high, while concurrently the burn rates are relatively low. For Mix 5 having cupric oxalate co-fuel, the volumetric gas yield is too low. For Mix 6 having melamine cyanurate as the co-fuel, the burning rate is acceptable, while the burn rate slope is relatively small.

EXAMPLE 2

A comparison of the properties of the formulations containing a melamine oxalate compound and other cool burning co-fuels similar to melamine oxalate are shown in Table 2 below. Four gas generant mixes are prepared with the formulations specified and tested for purposes of comparison. Mix 7 contains melamine oxalate (dimelamine trioxylate), while Mixes 8-10 contain alternative co-fuels that appear to provide cool burning gas generants. The slagging agent is glass fibers and the co-oxidizer is ammonium perchlorate. Flame combustion temperature ($T_c$) K, gas yield ($G_n$) in moles/100 g, volumetric gas yield ($G_v$) in moles 100 $cm^3$, mass density, linear burn rate ($R_b$) at 21 MPa, and slope of pressure sensitivity (n) are measured.

The burning rate of Mix 7 in Table 1 is lower than the desired burn rate of at least about 18 mm/second; however, the measured burning rates are from hand mixes, which are typically lower than burning rates obtained in the spray dry production process. Thus, like the burn rates in Table 1, the burn rates in Table 2 do not necessarily represent enhanced burn rates that will be achieved from production processes, but are provided for comparison purposes.

TABLE 2

| Property | Mix 7 | Mix 8 | Mix 9 | Mix 10 |
|---|---|---|---|---|
| % bCN | 55.47 | 50.04 | 63.44 | 53.74 |
| % $GuNO_3$ | 26.03 | 29.76 | 15.93 | 18.5 |
| % Co-fuel | 16<br>2:3 melamine oxalate (dimelamine trioxylate) | 11.25<br>urea oxalate | 18.13<br>Melamine cyanurate | 18.5<br>Biuret oxalate |
| % Slagging Agent | 1 | 1 | 1 | 1 |
| % Co-oxidizer | 1.5 | 1.5 | 1.5 | 1.5 |
| $T_c$ K | 1520 | 1520 | 1520 | 1520 |
| $G_n$ moles/100 g | 2.6 | 2.82 | 2.41 | 2.66 |
| Density g/$cm^3$ | 2.24 | 2.17 | 2.41 | 2.66 |
| $G_v$ moles/100 $cm^3$ | 5.83 | 6.12 | 5.81 | 5.88 |
| $R_b$ at 10 MPa mm/sec | 13.84 | 11.34 | 9.6 | 13.81 |
| Slope | 0.344 | 0.468 | 0.313 | 0.401 |

As shown in Table 2, melamine oxalate in Mix 7 (having dimelamine trioxylate co-fuel) meets various goals of high gas yield and good ballistic properties at cool combustion flame temperatures, including a high burn rate and low burn rate slope. For Mixes 8 and 10 having urea oxalate and biuret oxalate as the co-fuel, the pressure sensitivity/slopes are too high. For Mix 9 having melamine cyanurate co-fuel, the burn rate is too low.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cool burning gas generant composition for an automotive inflatable restraint system comprising:

a melamine monoxalate compound having a molar ratio of melamine to oxalic acid of about 1:1;

guanidine nitrate; and basic copper nitrate, wherein the gas generant composition has a maximum flame temperature at combustion ($T_c$) of less than or equal to about 1600K (1,327° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

2. A cool burning gas generant composition for an automotive inflatable restraint system comprising:

a dimelamine trioxalate compound, wherein the dimelamine trioxalate compound having a molar ratio of melamine to oxalic acid of about 2:3;

guanidine nitrate; and basic copper nitrate, wherein the gas generant composition has a maximum flame temperature at combustion ($T_c$) of less than or equal to about 1520K (1,247° C.), a linear burn rate of greater than or equal to about 18 mm per second at a pressure of about 10 megapascals (MPa), a gas yield of the gas generant of greater than or equal to about 5.7 moles/100 $cm^3$, and a linear burn rate pressure exponent of less than or equal to about 0.35.

3. The cool burning gas generant composition of claim 1 having a maximum flame temperature at combustion ($T_c$) of greater than or equal to about 1400K (1,127° C.) to less than or equal to about 1600K (1,327° C.).

4. The cool burning gas generant composition of claim 1, wherein the melamine monoxalate compound is present at greater than or equal to about 5% by weight to less than or equal to about 30% by weight of the total gas generant composition.

5. The cool burning gas generant composition of claim 1, wherein the guanidine nitrate is present at greater than or equal to about 10% to less than or equal to about 50% by weight of the gas generant composition.

6. The cool burning gas generant composition of claim 1, wherein the basic copper nitrate is present at greater than or equal to about 30% to less than or equal to about 70% by weight of the gas generant composition.

7. The cool burning gas generant composition of claim 1, wherein the melamine monoxalate compound is present at greater than or equal to about 5% by weight to less than or equal to about 30% by weight of the total gas generant composition, the guanidine nitrate is present at greater than or equal to about 10% to less than or equal to about 50% by weight of the total gas generant composition; the basic copper nitrate is present at greater than or equal to about 30% to less than or equal to about 70% by weight of the total gas generant composition; and greater than or equal to 0% to less than or equal to about 10% by weight of the total gas generant composition of one or more gas generant additives.

8. The cool burning gas generant composition of claim 2, wherein the dimelamine trioxalate compound is present at greater than or equal to about 5% by weight to less than or equal to about 30% by weight of the total gas generant composition.

9. The cool burning gas generant composition of claim 2, wherein the guanidine nitrate is present at greater than or equal to about 10% to less than or equal to about 50% by weight of the gas generant composition.

10. The cool burning gas generant composition of claim 2, wherein the basic copper nitrate is present at greater than or equal to about 30% to less than or equal to about 70% by weight of the gas generant composition.

11. The cool burning gas generant composition of claim 2, wherein the dimelamine trioxalate compound is present at greater than or equal to about 5% by weight to less than or equal to about 30% by weight of the total gas generant composition, the guanidine nitrate is present at greater than or equal to about 10% to less than or equal to about 50% by weight of the total gas generant composition; the basic copper nitrate is present at greater than or equal to about 30% to less than or equal to about 70% by weight of the total gas generant composition; and greater than or equal to 0% to less than or equal to about 10% by weight of the total gas generant composition of one or more gas generant additives.

* * * * *